United States Patent
Maruyama et al.

(10) Patent No.: US 11,202,750 B2
(45) Date of Patent: Dec. 21, 2021

(54) NON-STICKY STABLE COMPOSITION

(71) Applicant: L'OREAL, Paris (FR)

(72) Inventors: Kazuhiko Maruyama, Kawasaki (JP); Sho Watanabe, Kawasaki (JP)

(73) Assignee: L'OREAL, Paris (FR)

( * ) Notice: Subject to any disclaimer, the term of this patent is extended or adjusted under 35 U.S.C. 154(b) by 212 days.

(21) Appl. No.: 16/345,996

(22) PCT Filed: Nov. 24, 2017

(86) PCT No.: PCT/JP2017/043223
§ 371 (c)(1),
(2) Date: Apr. 29, 2019

(87) PCT Pub. No.: WO2018/105503
PCT Pub. Date: Jun. 14, 2018

(65) Prior Publication Data
US 2020/0054545 A1    Feb. 20, 2020

(30) Foreign Application Priority Data

Dec. 9, 2016  (JP) .............................. JP2016-239113

(51) Int. Cl.
| | | |
|---|---|---|
| *A61Q 5/00* | (2006.01) | |
| *A61K 8/86* | (2006.01) | |
| *A61K 8/06* | (2006.01) | |
| *A61K 8/39* | (2006.01) | |
| *A61K 8/46* | (2006.01) | |
| *A61K 8/58* | (2006.01) | |
| *A61K 8/92* | (2006.01) | |
| *A61Q 19/00* | (2006.01) | |

(52) U.S. Cl.
CPC ................ *A61K 8/86* (2013.01); *A61K 8/062* (2013.01); *A61K 8/39* (2013.01); *A61K 8/466* (2013.01); *A61K 8/585* (2013.01); *A61K 8/92* (2013.01); *A61Q 19/00* (2013.01); *A61K 2800/596* (2013.01)

(58) Field of Classification Search
CPC . A61K 8/062; A61K 8/06; A61K 8/86; A61K 8/39; A61K 8/064; A61K 8/92; A61K 8/25; A61K 8/585; A61K 8/463; A61K 8/89; A61K 2800/596
USPC ....................................... 424/70.1
See application file for complete search history.

(56) References Cited

U.S. PATENT DOCUMENTS

2008/0148495 A1 *  6/2008  Quadir .................. A61K 8/416
8/409

FOREIGN PATENT DOCUMENTS

| EP | 2786745 A1 * | 10/2012 | ............... A61K 8/86 |
|---|---|---|---|
| EP | 2786745 A1 | 10/2014 | |
| JP | 2003-300855 A | 10/2003 | |
| JP | 2007-153858 A | 6/2007 | |
| JP | 2011-073992 A | 4/2011 | |
| JP | 2012-184167 A | 9/2012 | |
| JP | 2015-063483 A | 4/2015 | |
| KR | 10-1467740 B1 | 12/2014 | |
| WO | 2016/098788 A1 | 6/2016 | |
| WO | WO 2016/098788 A1 * | 6/2016 | ............... A61K 8/39 |

OTHER PUBLICATIONS

Databases accession No. 3475725 (Nov. 2015).*
International Search Report dated Mar. 2, 2018 for International Application No. PCT/JP2017/043223.
Database GNPD [online] MINTEL; Nov. 1, 2015 (Nov. 1, 2015), laboratoires Dr N.G. Payot: "Jour Total Youth Enhancing Care", XP-002778090, Database accession No. 3475725.
Database GNPD [online] MINTEL; Feb. 1, 2015 (Feb. 1, 2015), Amorepacific: "Toner", XP-002778091, Database accession No. 2959667.
Database GNPD [online] MINTEL; L'Oréal: "Micronized Centella Essence Water", XP-002778092, Database accession No. 5121483.
KIPO, Office Action for the corresponding Korean patent application No. 10-2019-7013646, dated Sep. 21, 2020, with English translation.
Payot, "Supreme Jeunesse Jour Total Youth Day Cream 50 ml," Amazon.co.uk, Luxury Beauty (May 12, 2016).

* cited by examiner

*Primary Examiner* — Eisa B Elhilo
(74) *Attorney, Agent, or Firm* — Lucas & Mercanti, LLP

(57) ABSTRACT

A composition contains: (a) at least one oil; (b) at least one polyglyceryl fatty acid ester; (c) at least one polyoxyalkylenated organosilicon compound; (d) at least one nonionic surfactant other than the (b) polyglyceryl fatty acid ester; and (e) at least one anionic surfactant. An embodiment according to the present invention is a composition that provides no sticky feeling or a reduced sticky feeling to the touch, and is stable, in particular stable over time and/or under elevated temperature, although the composition includes a polyglyceryl fatty acid ester.

14 Claims, No Drawings

NON-STICKY STABLE COMPOSITION

CROSS-REFERENCE TO RELATED APPLICATIONS

This application is a 371 of PCT/JP2017/043223 filed on Nov. 24, 2017, which claims benefit of Japanese Patent Application No. 2016-239113 filed on Dec. 9, 2016, each of which is hereby incorporated by reference in its entirety.

TECHNICAL FIELD

The present invention relates to a composition, preferably a cosmetic or dermatological composition, which is non-sticky and stable.

BACKGROUND ART

Compositions including polyglyceryl fatty acid esters have been known in the fields of cosmetics and dermatology. Polyglyceryl fatty acid esters can function as surfactants, and therefore, they may be used to prepare, typically, emulsions such as oil-in-water (O/W) or water-in-oil (W/O) emulsions.

For example, JP-A-2007-153858, JP-A-2003-300855, JP-A-2012-184167 and JP-A-2011-73992 disclose emulsions which are formed by using a polyglyceryl fatty acid ester as a surfactant.

However, compositions including a polyglyceryl fatty acid ester often provide a sticky feeling to the touch and tend to be unstable, in particular unstable over time and/or under elevated temperature.

WO 2016/098788 discloses a composition comprising an oil, a polyglyceryl fatty acid ester, a silicone elastomer and a polysaccharide. The composition disclosed in WO 2016/098788 provides less sticky feeling to the touch and is stable.

There is still a need for a new approach to reduce a sticky feeling to the touch of a composition comprising a polyglyceryl fatty acid ester and to make the composition stable.

DISCLOSURE OF INVENTION

An objective of the present invention is to provide a composition which provides no sticky feeling or a reduced sticky feeling after application and which is stable, in particular stable over time and/or under elevated temperature, even if the composition includes a polyglyceryl fatty acid ester and silicones.

The above objective of the present invention can be achieved by a composition comprising:

(a) at least one oil;
(b) at least one polyglyceryl fatty acid ester;
(c) at least one polyoxyalkylenated organosilicon compound;
(d) at least one nonionic surfactant other than the (b) polyglyceryl fatty acid ester; and
(e) at least one anionic surfactant.

The (a) oil may comprise at least one ester oil.

The amount of the (a) oil in the composition according to the present invention may range from 0.01 to 30% by weight, preferably from 0.05 to 20% by weight, and more preferably from 0.1 to 10% by weight, relative to the total weight of the composition.

The (b) polyglyceryl fatty acid ester may have a polyglyceryl moiety derived from 2 to 10 glycerins, preferably 2 to 8 glycerins, and more preferably from 2 to 6 glycerins.

The (b) polyglyceryl fatty acid ester may be chosen from polyglyceryl monolaurate comprising 2 to 6 glycerol units, polyglyceryl mono(iso)stearate comprising 2 to 6 glycerol units, polyglyceryl monooleate comprising 2 to 6 glycerol units, and polyglyceryl dioleate comprising 2 to 6 glycerol units.

The amount of the (b) polyglyceryl fatty acid ester in the composition according to the present invention may range from 0.01 to 20% by weight, preferably from 0.05 to 15% by weight, and more preferably from 0.1 to 10% by weight, relative to the total weight of the composition.

The (c) polyoxyalkylenated organosilicon compound may be selected from polyoxyalkylenated silanes.

The amount of the (c) polyoxyalkylenated organosilicon compound in the composition according to the present invention may range from 0.01 to 20% by weight, preferably from 0.1 to 15% by weight, and more preferably from 1 to 10% by weight, relative to the total weight of the composition.

The (d) nonionic surfactant may be selected from polyoxyethylenated (1-40 EO) and polyoxypropylenated (1-30 PO) alkyl ($C_{16}$-$C_{30}$) ethers.

The amount of the (d) nonionic surfactant in the composition according to the present invention may range from 0.01 to 20% by weight, preferably from 0.05 to 15% by weight, and more preferably from 0.1 to 10% by weight, relative to the total weight of the composition.

The amount of the (e) anionic surfactant in the composition according to the present invention may range from 0.001 to 20% by weight, preferably from 0.005 to 15% by weight, and more preferably from 0.01 to 10% by weight, relative to the total weight of the composition.

The composition according to the present invention may further comprise water.

The weight ratio of (the total amounts of the (b) polyglyceryl fatty acid ester(s) and the (d) nonionic surfactant(s) other than the (b) polyglyceryl fatty acid ester(s))/the amount of the (a) oil(s)

in the composition according to the present invention may be 1.0 or more, preferably 1.5 or more, and more preferably 2.0 or more.

The weight ratio of the amount of the (c) polyoxyalkylenated organosilicon compound(s)/the amount of the (b) polyglyceryl fatty acid ester (s)

in the composition according to the present invention may be 3.5 or more, preferably 4.0 or more, and more preferably 4.5 or more.

The present invention also relates to a cosmetic process for treating a keratin substance, comprising the step of applying the composition according to the present invention to the keratin substance.

BEST MODE FOR CARRYING OUT THE INVENTION

After diligent research, the inventors have discovered a new approach to provide a composition which provides no sticky feeling or a reduced sticky feeling to the touch, even if the composition includes a polyglyceryl fatty acid ester, and which is stable, in particular stable over time and/or under elevated temperature, even if the composition includes a silicone, by using a specific combination of selected ingredients.

Thus, one aspect of the present invention is a composition comprising:

(a) at least one oil;
(b) at least one polyglyceryl fatty acid ester;
(c) at least one polyoxyalkylenated organosilicon compound;

(d) at least one nonionic surfactant other than the (b) polyglyceryl fatty acid ester; and (e) at least one anionic surfactant.

The composition according to the present invention includes a polyglyceryl fatty acid ester, but can provide no sticky feeling or a reduced sticky feeling to the touch. Therefore, the composition according to the present invention can provide an excellent feel during use, in particular on feeling of the skin after application of the composition.

The term "sticky" here means a property which provides a tacky feeling to the skin.

The composition according to the present invention is stable just after and a long time after the preparation of the composition, even under elevated temperature. Therefore, the composition according to the present invention is stable over time, and can be stored for a long period of time even under hot conditions such as in the summer.

Hereinafter, the composition according to the present invention will be explained in a more detailed manner.

[Oil]

The composition according to the present invention comprises (a) at least one oil. A single type of oil may be used, but two or more different types of oils may be used in combination.

Here, "oil" means a fatty compound or substance which is in the form of a liquid or a paste (non-solid) at room temperature (25° C.) under atmospheric pressure (760 mmHg). As the (a) oil(s), those generally used in cosmetics can be used alone or in combination thereof. These oils may be volatile or non-volatile.

The (a) oil may be a non-polar oil such as a hydrocarbon oil, a silicone oil, or the like; a polar oil such as a plant or animal oil and an ester oil or an ether oil; or a mixture thereof.

The (a) oil may be selected from the group consisting of oils of plant or animal origin, synthetic oils, silicone oils, hydrocarbon oils and fatty alcohols.

As examples of plant oils, mention may be made of, for example, linseed oil, camellia oil, macadamia nut oil, corn oil, mink oil, olive oil, avocado oil, sasanqua oil, castor oil, safflower oil, jojoba oil, sunflower oil, almond oil, rapeseed oil, sesame oil, soybean oil, peanut oil, and mixtures thereof.

As examples of synthetic oils, mention may be made of alkane oils such as isododecane and isohexadecane, ester oils, ether oils, and artificial triglycerides.

The ester oils are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the present invention are derived is branched.

Among the monoesters of monoacids and of monoalcohols, mention may be made of ethyl palmitate, ethyl hexyl palmitate, isopropyl palmitate, dicaprylyl carbonate, alkyl myristates such as isopropyl myristate or ethyl myristate, isocetyl stearate, 2-ethylhexyl isononanoate, isononyl isononanoate, isodecyl neopentanoate and isostearyl neopentanoate.

Esters of $C_4$-$C_{22}$ dicarboxylic or tricarboxylic acids and of $C_1$-$C_{22}$ alcohols, and esters of monocarboxylic, dicarboxylic or tricarboxylic acids and of non-sugar $C_4$-$C_{26}$ dihydroxy, trihydroxy, tetrahydroxy or pentahydroxy alcohols may also be used.

Mention may especially be made of: diethyl sebacate; isopropyl lauroyl sarcosinate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

As ester oils, one can use sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters, as well as pentaerythrityl tetraethyl hexanoate.

More particularly, use is made of monoesters and diesters and especially sucrose, glucose or methylglucose monooleates or dioleates, stearates, behenates, oleopalmitates, linoleates, linolenates and oleostearates.

An example that may be mentioned is the product sold under the name Glucate® DO by the company Amerchol, which is a methylglucose dioleate.

As examples of preferable ester oils, mention may be made of, for example, diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, dicaprylyl carbonate, isopropyl lauroyl sarcosinate, isononyl isononanoate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrithyl tetra(2-ethylhexanoate), 2-ethylhexyl succinate, diethyl sebacate, and mixtures thereof.

As examples of artificial triglycerides, mention may be made of, for example, capryl caprylyl glycerides, glyceryl trimyristate, glyceryl tripalmitate, glyceryl trilinolenate, glyceryl trilaurate, glyceryl tricaprate, glyceryl tricaprylate, glyceryl tri(caprate/caprylate) and glyceryl tri(caprate/caprylate/linolenate).

As examples of silicone oils, mention may be made of, for example, linear organopolysiloxanes such as dimethylpolysiloxane, methylphenylpolysiloxane, methylhydrogenpolysiloxane, and the like; cyclic organopolysiloxanes such as cyclohexasiloxane, octamethylcyclotetrasiloxane, decamethylcyclopentasiloxane, dodecamethylcyclohexasiloxane, and the like; and mixtures thereof.

Preferably, silicone oil is chosen from liquid polydialkylsiloxanes, especially liquid polydimethylsiloxanes (PDMS) and liquid polyorganosiloxanes comprising at least one aryl group.

These silicone oils may also be organomodified. The organomodified silicones that can be used in accordance with the present invention are silicone oils as defined above and comprise in their structure one or more organofunctional groups attached via a hydrocarbon-based group.

Organopolysiloxanes are defined in greater detail in Walter Noll's *Chemistry and Technology of Silicones* (1968), Academic Press. They may be volatile or non-volatile.

When they are volatile, the silicones are more particularly chosen from those having a boiling point of between 60° C. and 260° C., and even more particularly from:
(i) cyclic polydialkylsiloxanes comprising from 3 to 7 and preferably 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, Silbione® 70045 V5 by Rhodia, and dodecamethylcyclopentasiloxane sold under the name Silsoft 1217 by Momentive Performance Materials, and mixtures thereof. Mention may also be made of cyclocopolymers of the type such as dimethylsiloxane/methylalkylsiloxane, such as Silicone Volatile® FZ 3109 sold by the company Union Carbide, of formula:

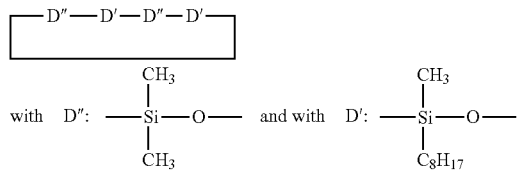

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;
(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, Volatile Silicone Fluids for Cosmetics. The viscosity of the silicones is measured at 25° C. according to ASTM standard 445 Appendix C.

Non-volatile polydialkylsiloxanes may also be used. These non-volatile silicones are more particularly chosen from polydialkylsiloxanes, among which mention may be made mainly of polydimethylsiloxanes containing trimethylsilyl end groups.

Among these polydialkylsiloxanes, mention may be made, in a non-limiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 mm$^2$/s;

the Viscasil® oils from General Electric and certain oils of the SF series (SF 96, SF 18) from General Electric.

Mention may also be made of polydimethylsiloxanes containing dimethylsilanol end groups known under the name dimethiconol (CTFA), such as the oils of the 48 series from the company Rhodia.

Among the silicones containing aryl groups are polydiarylsiloxanes, especially polydiphenylsiloxanes and polyalkylarylsiloxanes. Examples that may be mentioned include the products sold under the following names:

the Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

certain oils of the SF series from General Electric, such as SF 1023, SF 1154, SF 1250 and SF 1265.

The organomodified liquid silicones may especially contain polyethyleneoxy and/or polypropyleneoxy groups. Mention may thus be made of the silicone KF-6017 proposed by Shin-Etsu, and the oils Silwet® L722 and L77 from the company Union Carbide.

Hydrocarbon oils may be chosen from:
linear or branched, optionally cyclic, $C_6$-$C_{16}$ lower alkanes. Examples that may be mentioned include hexane, undecane, dodecane, tridecane, and isoparaffins, for instance isohexadecane, isododecane and isodecane; and linear or branched hydrocarbons containing more than 16 carbon atoms, such as liquid paraffins, liquid petroleum jelly, polydecenes and hydrogenated polyisobutenes such as Parleam®, and squalane.

As preferable examples of hydrocarbon oils, mention may be made of, for example, linear or branched hydrocarbons such as isohexadecane, isododecane, squalane, mineral oil (e.g., liquid paraffin), paraffin, vaseline or petrolatum, naphthalenes, and the like; hydrogenated polyisobutene, isoeicosan, and decene/butene copolymer; and mixtures thereof.

The term "fatty" in the fatty alcohol means the inclusion of a relatively large number of carbon atoms. Thus, alcohols which have 4 or more, preferably 6 or more, and more preferably 12 or more carbon atoms are encompassed within the scope of fatty alcohols. The fatty alcohol may be saturated or unsaturated. The fatty alcohol may be linear or branched.

The fatty alcohol may have the structure R—OH wherein R is chosen from saturated and unsaturated, linear and branched radicals containing from 4 to 40 carbon atoms, preferably from 6 to 30 carbon atoms, and more preferably from 12 to 20 carbon atoms. In at least one embodiment, R may be chosen from $C_{12}$-$C_{20}$ alkyl and $C_{12}$-$C_{20}$ alkenyl groups. R may be or may not be substituted with at least one hydroxyl group.

As examples of the fatty alcohol, mention may be made of lauryl alcohol, cetyl alcohol, stearyl alcohol, isostearyl alcohol, behenyl alcohol, undecylenyl alcohol, myristyl alcohol, octyldodecanol, hexyldecanol, oleyl alcohol, linoleyl alcohol, palmitoleyl alcohol, arachidonyl alcohol, erucyl alcohol, and mixtures thereof.

It is preferable that fatty alcohol be a saturated fatty alcohol.

Thus, the fatty alcohol may be selected from straight or branched, saturated or unsaturated $C_6$-$C_{30}$ alcohols, preferably straight or branched, saturated $C_6$-$C_{30}$ alcohols, and more preferably straight or branched, saturated $C_{12}$-$C_{20}$ alcohols.

The term "saturated fatty alcohol" here means an alcohol having a long aliphatic saturated carbon chain. It is preferable that the saturated fatty alcohol be selected from any linear or branched, saturated $C_6$-$C_{30}$ fatty alcohols. Among the linear or branched, saturated $C_6$-$C_{30}$ fatty alcohols, linear or branched, saturated $C_{12}$-$C_{20}$ fatty alcohols may preferably be used. Any linear or branched, saturated $C_{16}$-$C_{20}$ fatty alcohols may be more preferably used. Branched $C_{16}$-$C_{20}$ fatty alcohols may be even more preferably used.

As examples of saturated fatty alcohols, mention may be made of lauryl alcohol, cetyl alcohol, stearyl alcohol, isostearyl alcohol, behenyl alcohol, undecylenyl alcohol, myristyl alcohol, octyldodecanol, hexyldecanol, and mixtures thereof. In one embodiment, cetyl alcohol, stearyl alcohol, octyldodecanol, hexyldecanol, or a mixture thereof (e.g., cetearyl alcohol) as well as behenyl alcohol, can be used as a saturated fatty alcohol.

According to at least one embodiment, the fatty alcohol used in the composition according to the present invention is preferably chosen from octyldodecanol, hexyldecanol and mixtures thereof.

It is preferable that the (a) oil be chosen from ester oils and fatty alcohols, more preferably ester oils.

In other words, it is preferable that the (a) oil comprise at least one ester oil.

It may be preferable that the (a) oil be chosen from oils with molecular weight below 600 g/mol.

The amount of the (a) oil(s) in the composition according to the present invention may be 0.01% by weight or more, preferably 0.05% by weight or more, and more preferably 0.1% by weight or more, relative to the total weight of the composition. It may be even more preferable that the amount of the (a) oil(s) in the composition according to the present invention be 0.5% by weight or more, relative to the total weight of the composition.

On the other hand, the amount of the (a) oil(s) in the composition according to the present invention may be 30% by weight or less, preferably 20% by weight or less, and more preferably 10% by weight or less, relative to the total weight of the composition. It may be even more preferable that the amount of the (a) oil(s) in the composition according to the present invention be 5% by weight or less, relative to the total weight of the composition.

The amount of the (a) oil(s) in the composition according to the present invention may range from 0.01 to 30% by weight, preferably from 0.05 to 20% by weight, more preferably from 0.1 to 10% by weight, relative to the total weight of the composition. It may be even more preferable that the amount of the (a) oil(s) in the composition according to the present invention be from 0.5% to 5% by weight, relative to the total weight of the composition.

[Polyglyceryl Fatty Acid Ester]

The composition according to the present invention comprises (b) at least one polyglyceryl fatty acid ester. A single type of polyglyceryl fatty acid ester may be used, but two or more different types of polyglyceryl fatty acid ester may be used in combination.

It is preferable that the (b) polyglyceryl fatty acid ester have a polyglycerol moiety derived from 2 to 10 glycerols, more preferably from 2 to 8 glycerols, and further more preferably from 2 to 6 glycerols.

The (b) polyglyceryl fatty acid ester may have an HLB (Hydrophilic Lipophilic Balance) value of from 7.0 to 16.0, preferably from 8.0 to 15.0, and more preferably from 10.0 to 13.0. If two or more polyglyceryl fatty acid esters are used, the HLB value is determined by the weight average of the HLB values of all the polyglyceryl fatty acid esters.

The (b) polyglyceryl fatty acid ester may be chosen from the mono, di and tri esters of saturated or unsaturated acid, preferably saturated acid, including 2 to 30 carbon atoms, preferably 6 to 30 carbon atoms, and more preferably 8 to 30 carbon atoms, such as lauric acid, oleic acid, stearic acid, isostearic acid, capric acid, caprylic acid, and myristic acid.

The (b) polyglyceryl fatty acid ester may be selected from the group consisting of PG2 caprylate, PG2 sesquicaprylate, PG2 dicaprylate, PG2 tricaprylate, PG2 caprate, PG2 sesquicaprate, PG2 dicaprate, PG2 tricaprate, PG2 laurate, PG2 sesquilaurate, PG2 dilaurate, PG2 trilaurate, PG2 myristate, PG2 sesquimyristate, PG2 dimyristate, PG2 trimyristate, PG2 stearate, PG2 sesquistearate, PG2 distearate, PG2 tristearate, PG2 isostearate, PG2 sesquiisostearate, PG2 diisostearate, PG2 triisostearate, PG2 oleate, PG2 sesquioleate, PG2 dioleate, PG2 trioleate, PG3 caprylate, PG3 sesquicaprylate, PG3 dicaprylate, PG3 tricaprylate, PG3 caprate, PG3 sesquicaprate, PG3 dicaprate, PG3 tricaprate, PG3 laurate, PG3 sesquilaurate, PG3 dilaurate, PG3 trilaurate, PG3 myristate, PG3 sesquimyristate, PG3 dimyristate, PG3 trimyristate, PG3 stearate, PG3 sesquistearate, PG3 distearate, PG3 tristearate, PG3 isostearate, PG3 sesquiisostearate, PG3 diisostearate, PG3 triisostearate, PG3 oleate, PG3 sesquioleate, PG3 dioleate, PG3 trioleate, PG4 caprylate, PG4 sesquicaprylate, PG4 dicaprylate, PG4 tricaprylate, PG4 caprate, PG4 sesquicaprate, PG4 dicaprate, PG4 tricaprate, PG4 laurate, PG4 sesquilaurate, PG4 dilaurate, PG4 trilaurate, PG4 myristate, PG4 sesquimyristate, PG4 dimyristate, PG4 trimyristate, PG4 stearate, PG4 sesquistearate, PG4 distearate, PG4 tristearate, PG4 isostearate, PG4 sesquiisostearate, PG4 diisostearate, PG4 triisostearate, PG4 oleate, PG4 sesquioleate, PG4 dioleate, PG4 trioleate, PG5 caprylate, PG5 sesquicaprylate, PG5 dicaprylate, PG5 tricaprylate, PG5 tetracaprylate, PG5 caprate, PG5 sesquicaprate, PG5 dicaprate, PG5 tricaprate, PG5 tetracaprate, PG5 laurate, PG5 sesquilaurate, PG5 dilaurate, PG5 trilaurate, PG5 tetralaurate, PG5 myristate, PG5 sesquimyristate, PG5 dimyristate, PG5 trimyristate, PG5 tetramyristate, PG5 stearate, PG5 sesquistearate, PG5 distearate, PG5 tristearate, PG5 tetrastearate, PG5 isostearate, PG5 sesquiisostearate, PG5 diisostearate, PG5 triisostearate, PG5 tetraisostearate, PG5 oleate, PG5 sesquioleate, PG5 dioleate, PG5 trioleate, PG5 tetraoleate, PG6 caprylate, PG6 sesquicaprylate, PG6 dicaprylate, PG6 tricaprylate, PG6 tetracaprylate, PG6 pentacaprylate, PG6 caprate, PG6 sesquicaprate, PG6 dicaprate, PG6 tricaprate, PG6 tetracaprate, PG6 pentacaprate, PG6 laurate, PG6 sesquilaurate, PG6 dilaurate, PG6 trilaurate, PG6 tetralaurate, PG6 pentalaurate, PG6 myristate, PG6 sesquimyristate, PG6 dimyristate, PG6 trimyristate, PG6 tetramyristate, PG6 pentamyristate, PG6 stearate, PG6 sesquistearate, PG6 distearate, PG6 tristearate, PG6 tetrastearate, PG6 pentastearate, PG6 isostearate, PG6 sesquiisostearate, PG6 diisostearate, PG6 triisostearate, PG6 tetraisostearate, PG6 pentaisostearate, PG6 oleate, PG6 sesquioleate, PG6 dioleate, PG6 trioleate, PG6 tetraoleate, PG6 pentaoleate, PG10 caprylate, PG10 sesquicaprylate, PG10 dicaprylate, PG10 tricaprylate, PG10 tetracaprylate, PG10 pentacaprylate, PG10 hexacaprylate, PG10 caprate, PG10 sesquicaprate, PG10 dicaprate, PG10 tricaprate, PG10 tetracaprate, PG10 pentacaprate, PG10 hexacaprate, PG10 laurate, PG10 sesquilaurate, PG10 dilaurate, PG10 trilaurate, PG10 tetralaurate, PG10 pentalaurate, PG10 hexalaurate, PG10 myristate, PG10 sesquimyristate, PG10 dimyristate, PG10 trimyristate, PG10 tetramyristate, PG10 pentamyristate, PG10 hexamyristate, PG10 stearate, PG10 sesquistearate, PG10 distearate, PG10 tristearate, PG10 tetrastearate, PG10 pentastearate, PG10 hexastearate, PG10 isostearate, PG10 sesquiisostearate, PG10 diisostearate, PG10 triisostearate, PG10 tetraisostearate, PG10 pentaisostearate, PG10 hexaisostearate, PG10 oleate, PG10 sesquioleate, PG10 dioleate, PG10 trioleate, PG10 tetraoleate, PG10 pentaoleate, and PG10 hexaoleate.

It is preferable that the (b) polyglyceryl fatty acid ester be chosen from:

polyglyceryl monolaurate comprising 2 to 6 glycerol units, polyglyceryl mono(iso)stearate comprising 2 to 6 glycerol units, polyglyceryl monooleate comprising 2 to 6 glycerol units, and polyglyceryl dioleate comprising 2 to 6 glycerol units.

In one embodiment, the (b) polyglyceryl fatty acid ester raw material may be chosen from a mixture of polyglyceryl fatty acid esters, preferably with a polyglyceryl moiety derived from 2 to 10 glycerins, more preferably 2 to 6 glycerins, wherein the mixture preferably comprises 30% by weight or more of a polyglyceryl fatty acid ester with a polyglyceryl moiety consisting of 2 to 6 glycerins.

It may be preferable than the (b) polyglyceryl fatty acid ester raw material comprise esters of a fatty acid and polyglycerine containing 70% or more of polyglycerine whose polymerization degree is 2 or more, preferably esters of a fatty acid and polyglycerine containing equal to or more than 60% of polyglycerine whose polymerization degree is between 2 and 6, and more preferably esters of a fatty acid and polyglycerine containing equal to or more than 30% of polyglycerine whose polymerization degree is 2 to 6.

The amount of the (b) polyglyceryl fatty acid ester(s) in the composition according to the present invention may be 0.01% by weight or more, preferably 0.05% by weight or more, and more preferably 0.1% by weight or more, relative to the total weight of the composition. It may be even more preferable that the amount of the (b) polyglyceryl fatty acid ester(s) in the composition according to the present invention be 0.5% by weight or more, relative to the total weight of the composition.

On the other hand, the amount of the (b) polyglyceryl fatty acid ester(s) in the composition according to the present invention may be 20% by weight or less, preferably 15% by weight or less, and more preferably 10% by weight or less, relative to the total weight of the composition. It may be even more preferable that the amount of the (b) polyglyceryl fatty acid ester(s) in the composition according to the present invention be 5% by weight or less, relative to the total weight of the composition.

The amount of the (b) polyglyceryl fatty acid ester(s) in the composition according to the present invention may range from 0.01 to 20% by weight, preferably from 0.05 to 15% by weight, more preferably from 0.1 to 10% by weight, relative to the total weight of the composition. It may be even more preferable that the amount of the (b) polyglyceryl fatty acid ester(s) in the composition according to the present invention be from 0.5% to 5% by weight, relative to the total weight of the composition.

[Polyoxyalkylenated Organosilicon Compound]

The composition according to the present invention comprises (c) at least one polyoxyalkylenated organosilicon compound. A single type of polyoxyalkylenated organosilicon compound may be used, but two or more different types of polyoxyalkylenated organosilicon compounds may be used in combination.

The (c) polyoxyalkylenated organosilicon compound is different from the (a) oil.

It may be preferable that the (c) polyoxyalkylenated organosilicon compound be in the form of a wax. Thus, It may be preferable that the (c) polyoxyalkylenated organosilicon compound have a melting point of greater than 30° C., and more preferably, greater than 35° C.

The (c) polyoxyalkylenated organosilicon compound has at least one silicon atom and at least one polyoxyalkylene moiety such as a polyoxyethylene and a polyoxypropylene moiety.

The (c) polyoxyalkylenated organosilicon compound may or may not be crosslinked. Preferably, the (c) polyoxyalkylenated organosilicon compound is not crosslinked.

It is more preferable that the (c) polyoxyalkylenated organosilicon compound be water-dispersible. Accordingly, it is more preferable that the (c) polyoxyalkylenated organosilicon compound be selected from polyoxyalkylenated silanes and polyoxyalkylenated silicones.

The polyoxyalkylenated silanes may be represented by the following formula (I):

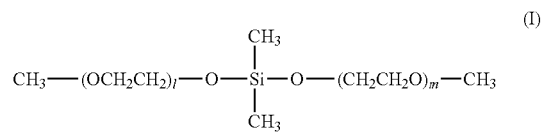

wherein l and m denote independently an integer from 10 to 25, and preferably from 15 to 20.

As examples of the above compound, mention may be made of Bis-PEG-18 methyl ether dimethyl silane such as Dow Corning 2501 Cosmetic Wax sold by Dow Corning Toray and SM4110P sold by KCC Corporation.

The polyoxyalkylenated silicones may be dimethicone copolyols.

The dimethicone copolyol employed according to the present invention may be an oxyethylenated and/or oxypropylenated polydimethyl(methyl)siloxane.

Use may be made, as dimethicone copolyol, of those corresponding to the following formula (II):

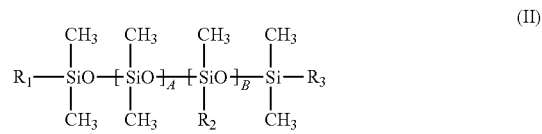

in which:

$R_1$, $R_2$ and $R_3$ represent, independently of one another, a $C_1$-$C_6$ alkyl radical or a —$(CH_2)_x$—$(OCH_2CH_2)_y$—$(OCH_2CH_2CH_2)_z$—$OR_4$ radical, at least one $R_1$, $R_2$ or $R_3$ radical not being an alkyl radical; $R_4$ being a hydrogen, a $C_1$-$C_3$ alkyl radical or a $C_2$-$C_4$ acyl radical;

A is an integer ranging from 0 to 200;

B is an integer ranging from 0 to 50;

provided that A and B are not equal to zero at the same time;

x is an integer ranging from 1 to 6;
y is an integer ranging from 1 to 30; and
z is an integer ranging from 0 to 5.

According to a preferred embodiment of the invention, in the compound of formula (II), $R_1$-$R_3$=methyl radical, x is an integer ranging from 2 to 6 and y is an integer ranging from 4 to 30. $R_4$ is in particular a hydrogen.

Mention may be made, as examples of compounds of formula (II), of the compounds of formula (III):

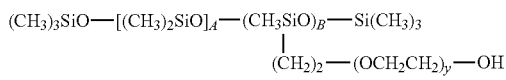

(III)

in which
A is an integer ranging from 20 to 105,
B is an integer ranging from 2 to 10, and
y is an integer ranging from 10 to 20.

Mention may also be made, as examples of silicone compounds of formula (II), of the compounds of formula (IV):

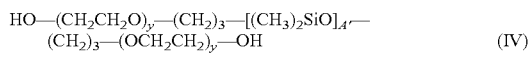

(IV)

in which A' and y are integers ranging from 10 to 20.

Use may be made, as dimethicone copolyol, of those sold under the names DC 5329, DC 7439-146, DC2-5695 and Q4-3667 by Dow Corning; and KF-6013, KF-6015, KF-6016, KF-6017 and KF-6028 by Shin-Etsu.

The compounds DC 5329, DC 7439-146 and DC2-5695 are compounds of formula (III) where, respectively, A is 22, B is 2 and y is 12; A is 103, B is 10 and y is 12; and A is 27, B is 3 and y is 12.

The amount of the (c) polyoxyalkylenated organosilicon compound(s) in the composition according to the present invention may be 0.01% by weight or more, preferably 0.1% by weight or more, and more preferably 1% by weight or more, relative to the total weight of the composition. It may be even more preferable that the amount of the (c) polyoxyalkylenated organosilicon compound(s) in the composition according to the present invention be 3% by weight or more, relative to the total weight of the composition.

On the other hand, the amount of the (c) polyoxyalkylenated organosilicon compound(s) in the composition according to the present invention may be 20% by weight or less, preferably 15% by weight or less, and more preferably 10% by weight or less, relative to the total weight of the composition. It may be even more preferable that the amount of the (c) polyoxyalkylenated organosilicon compound(s) in the composition according to the present invention be 8% by weight or less, relative to the total weight of the composition.

The amount of the (c) polyoxyalkylenated organosilicon compound(s) in the composition according to the present invention may range from 0.01 to 20% by weight, preferably from 0.1 to 15% by weight, more preferably from 1 to 10% by weight, relative to the total weight of the composition. It may be even more preferable that the amount of the (c) polyoxyalkylenated organosilicon compound(s) in the composition according to the present invention be from 3% to 8% by weight, relative to the total weight of the composition.

[Additional Nonionic Surfactant]

The composition according to the present invention comprises (d) at least one additional nonionic surfactant different from the above (b) polyglyceryl fatty acid ester. A single type of the additional nonionic surfactant may be used, but two or more different types of the additional nonionic surfactants may be used in combination.

The nonionic surfactants are compounds well known in and of themselves (see, e.g., in this regard, "Handbook of Surfactants" by M. R. Porter, Blackie & Son publishers (Glasgow and London), 1991, pp. 116-178). Thus, they can, for example, be chosen from alcohols, alpha-diols, alkylphenols and esters of fatty acids, these compounds being ethoxylated, propoxylated or glycerolated and having at least one fatty chain comprising, for example, from 8 to 30 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils of plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives; amine oxides such as ($C_{10}$-$C_{14}$)alkylamine oxides or N—($C_{10}$-$C_{14}$)acylaminopropylmorpholine oxides; silicone surfactants; and mixtures thereof.

The nonionic surfactants may preferably be chosen from monooxyalkylenated, polyoxyalkylenated, monoglycerolated or polyglycerolated nonionic surfactants. The oxyalkylene units are more particularly oxyethylene or oxypropylene units, or a combination thereof, and are preferably oxyethylene units.

Examples of monooxyalkylenated or polyoxyalkylenated nonionic surfactants that may be mentioned include:

monooxyalkylenated or polyoxyalkylenated ($C_8$-$C_{24}$)alkylphenols, saturated or unsaturated, linear or branched, monooxyalkylenated or polyoxyalkylenated $C_8$-$C_{30}$ alcohols, saturated or unsaturated, linear or branched, monooxyalkylenated or polyoxyalkylenated $C_8$-$C_{30}$ amides, esters of saturated or unsaturated, linear or branched, $C_8$-$C_{30}$ acids and of polyalkylene glycols, monooxyalkylenated or polyoxyalkylenated esters of saturated or unsaturated, linear or branched, $C_8$-$C_{30}$ acids and of sorbitol, saturated or unsaturated, monooxyalkylenated or polyoxyalkylenated plant oils, condensates of ethylene oxide and/or of propylene oxide, inter alia, alone or as mixtures.

The surfactants preferably contain a number of moles of ethylene oxide and/or of propylene oxide of between 1 and 100 and most preferably between 2 and 50. Advantageously, the nonionic surfactants do not comprise any oxypropylene units.

According to one of the embodiments of the present invention, the polyoxyalkylenated nonionic surfactants are chosen from polyoxyethylenated fatty alcohol (polyethylene glycol ether of fatty alcohol) and polyoxyethylenated fatty ester (polyethylene glycol ester of fatty acid).

Examples of polyoxyethylenated fatty alcohol (or $C_8$-$C_{30}$ alcohols) that may be mentioned include the adducts of ethylene oxide with lauryl alcohol, especially those containing from 9 to 50 oxyethylene units and more particularly those containing from 10 to 12 oxyethylene units (Laureth-10 to Laureth-12, as the CTFA names); the adducts of ethylene oxide with behenyl alcohol, especially those containing from 9 to 50 oxyethylene units (Beheneth-9 to Beheneth-50, as the CTFA names); the adducts of ethylene oxide with cetearyl alcohol (mixture of cetyl alcohol and stearyl alcohol), especially those containing from 10 to 30 oxyethylene units (Ceteareth-10 to Ceteareth-30, as the CTFA names); the adducts of ethylene oxide with cetyl alcohol, especially those containing from 10 to 30 oxyethylene units (Ceteth-10 to Ceteth-30, as the CTFA names); the adducts of ethylene oxide with stearyl alcohol, especially those containing from 10 to 30 oxyethylene units (Steareth-10 to Steareth-30, as the CTFA names); the adducts of ethylene oxide with isostearyl alcohol, especially those containing from 10 to 50 oxyethylene units (Isosteareth-10 to Isosteareth-50, as the CTFA names); and mixtures thereof.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols correspond to the following formula:

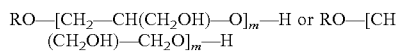

RO—[CH$_2$—CH(CH$_2$OH)—O]$_m$—H or RO—[CH(CH$_2$OH)—CH$_2$O]$_m$—H in which R represents a linear or branched $C_8$-$C_{40}$ and preferably $C_8$-$C_{30}$ alkyl or alkenyl radical, and m represents a number ranging from 1 to 30 and preferably from 1.5 to 10.

As examples of compounds that are suitable in the context of the present invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

Among the monoglycerolated or polyglycerolated alcohols, it is preferable to use the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

Examples of polyoxyethylenated fatty esters that may be mentioned include the adducts of ethylene oxide with esters of lauric acid, palmitic acid, stearic acid or behenic acid, and mixtures thereof, especially those containing from 9 to 100 oxyethylene units, such as PEG-9 to PEG-50 laurate (CTFA names: PEG-9 laurate to PEG-50 laurate); PEG-9 to PEG-50 palmitate (CTFA names: PEG-9 palmitate to PEG-50 palmitate); PEG-9 to PEG-50 stearate (CTFA names: PEG-9 stearate to PEG-50 stearate); PEG-9 to PEG-50 palmitostearate; PEG-9 to PEG-50 behenate (CTFA names: PEG-9 behenate to PEG-50 behenate); polyethylene glycol 100 EO monostearate (CTFA name: PEG-100 stearate); and mixtures thereof.

According to one of the embodiments of the present invention, the nonionic surfactant may be selected from esters of polyols with fatty acids with a saturated or unsaturated chain containing for example from 8 to 24 carbon atoms, preferably 12 to 22 carbon atoms, and polyoxyalkylenated derivatives thereof, preferably containing from 10 to 200, and more preferably from 10 to 100 oxyalkylene units, such as glyceryl esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; sorbitol esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; sugar (sucrose, maltose, glucose, fructose, and/or alkylglycose) esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; ethers of fatty alcohols; ethers of sugar and a $C_8$-$C_{24}$, preferably $C_{12}$-$C_{22}$, fatty alcohol or alcohols; and mixtures thereof.

As glyceryl esters of fatty acids, glyceryl stearate (glyceryl mono-, di- and/or tristearate) (CTFA name: glyceryl stearate) or glyceryl ricinoleate and mixtures thereof can be cited, and as polyoxyalkylenated derivatives thereof, mono-, di- or triester of fatty acids with a polyoxyalkylenated glycerol (mono-, di- or triester of fatty acids with a polyalkylene glycol ether of glycerol), preferably polyoxyethylenated glyceryl stearate (mono-, di- and/or tristearate), such as PEG-20 glyceryl stearate (mono-, di- and/or tristearate) can be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEGIN by Goldschmidt (CTFA name: glyceryl stearate SE), can also be used.

The sorbitol esters of $C_8$-$C_{24}$ fatty acids and polyoxyalkylenated derivatives thereof can be selected from sorbitan palmitate, sorbitan isostearate, sorbitan trioleate and esters of fatty acids and alkoxylated sorbitan containing for example from 20 to 100 EO, such as for example sorbitan monostearate (CTFA name: sorbitan stearate), sold by the company ICI under the name Span 60, sorbitan monopalmitate (CTFA name: sorbitan palmitate), sold by the company ICI under the name Span 40, and sorbitan tristearate 20 EO (CTFA name: polysorbate 65), sold by the company ICI under the name Tween 65, polyethylene sorbitan trioleate (polysorbate 85) or the compounds marketed under the trade names Tween 20 or Tween 60 by Uniqema.

As esters of fatty acids and glucose or alkylglucose, glucose palmitate, alkylglucose sesquistearates such as methylglucose sesquistearate, alkylglucose palmitates such as methylglucose or ethylglucose palmitate, methylglucoside fatty esters, the diester of methylglucoside and oleic acid (CTFA name: Methyl glucose dioleate), the mixed ester of methylglucoside and the mixture of oleic acid/hydroxystearic acid (CTFA name: Methyl glucose dioleate/hydroxystearate), the ester of methylglucoside and isostearic acid (CTFA name: Methyl glucose isostearate), the ester of methylglucoside and lauric acid (CTFA name: Methyl glucose laurate), the mixture of monoester and diester of methylglucoside and isostearic acid (CTFA name: Methyl glucose sesqui-isostearate), the mixture of monoester and diester of methylglucoside and stearic acid (CTFA name: Methyl glucose sesquistearate) and in particular the product marketed under the name Glucate SS by AMERCHOL, and mixtures thereof can be cited.

As ethoxylated ethers of fatty acids and glucose or alkylglucose, ethoxylated ethers of fatty acids and methylglucose, and in particular the polyethylene glycol ether of the diester of methylglucose and stearic acid with about 20 moles of ethylene oxide (CTFA name: PEG-20 methyl glucose distearate) such as the product marketed under the name Glucam E-20 distearate by AMERCHOL, the polyethylene glycol ether of the mixture of monoester and diester of methyl-glucose and stearic acid with about 20 moles of ethylene oxide (CTFA name: PEG-20 methyl glucose sesquistearate) and in particular the product marketed under the name Glucamate SSE-20 by AMERCHOL and that marketed under the name Grillocose PSE-20 by GOLDSCHMIDT, and mixtures thereof, can for example be cited.

As sucrose esters, saccharose palmito-stearate, saccharose stearate and saccharose monolaurate can for example be cited.

As sugar ethers, alkylpolyglucosides can be used, and for example decylglucoside such as the product marketed under the name MYDOL 10 by Kao Chemicals, the product marketed under the name PLANTAREN 2000 by Henkel, and the product marketed under the name ORAMIX NS 10 by Seppic, caprylyl/capryl glucoside such as the product marketed under the name ORAMIX CG 110 by Seppic or under the name LUTENSOL GD 70 by BASF, laurylglucoside such as the products marketed under the names PLANTAREN 1200 N and PLANTACARE 1200 by Henkel, coco-glucoside such as the product marketed under the name PLANTACARE 818/UP by Henkel, cetostearyl glucoside possibly mixed with cetostearyl alcohol, marketed for example under the 50 name MONTANOV 68 by Seppic, under the name TEGO-CARE CG90 by Goldschmidt and under the name EMULGADE KE3302 by Henkel, arachidyl glucoside, for example in the form of the mixture of arachidyl and behenyl alcohols and arachidyl glucoside marketed under the name MONTANOV 202 by Seppic, cocoylethylglucoside, for example in the form of the mixture (35/65) with cetyl and stearyl alcohols, marketed under the name MONTANOV 82 by Seppic, and mixtures thereof can in particular be cited.

Mixtures of glycerides of alkoxylated plant oils such as mixtures of ethoxylated (200 EO) palm and copra (7 EO) glycerides can also be cited.

The nonionic surfactant according to the present invention preferably contains alkenyl or branched $C_{12}$-$C_{22}$ acyl chain such as an oleyl or isostearyl group. More preferably, the nonionic surfactant according to the present invention is PEG-20 glyceryl triisostearate.

According to one of the embodiments of the present invention, the nonionic surfactant may be selected from polyoxyethylenated (1-40 EO) and polyoxypropylenated (1-30 PO) alkyl ($C_{16}$-$C_{30}$) ethers.

The polyoxyethylenated (1-40 EO) and polyoxypropylenated (1-30 PO) alkyl ($C_{16}$-$C_{30}$) ethers which may be used as surfactants in the nanoemulsion according to the present invention, may be selected from the group consisting of:

PPG-6 Decyltetradeceth-30; Polyoxyethlene (30) Polyoxypropylene (6) Tetradecyl Ether such as those sold as Nikkol PEN-4630 from Nikko Chemicals Co., PPG-6 Decyltetradeceth-12; Polyoxyethylene (12) Polyoxypropylene (6) Tetradecyl Ether such as those sold as Nikkol PEN-4612 from Nikko Chemicals Co., PPG-13 Decyltetradeceth-24; Polyoxyethylene (24) Polyoxypropylene (13) Decyltetradecyl Ether such as those sold as UNILUBE 50MT-2200B from NOF Corporation, PPG-6 Decyltetradeceth-20; Polyoxyethylene (20) Polyoxypropylene (6) Decyltetradecyl Ether such as those sold as Nikkol PEN-4620 from Nikko Chemicals Co., PPG-4 Ceteth-1; Polyoxyethylene (1) Polyoxypropylene (4) Cetyl Ether such as those sold as Nikkol PBC-31 from Nikko Chemicals Co., PPG-8 Ceteth-1; Polyoxyethylene (1) Polyoxypropylene (8) Cetyl Ether such as those sold as Nikkol PBC-41 from Nikko Chemicals Co., PPG-4 Ceteth-10; Polyoxyethylene (10) Polyoxypropylene (4) Cetyl Ether such as those sold as Nikkol PBC-33 from Nikko Chemicals Co., PPG-4 Ceteth-20; Polyoxyethylene (20) Polyoxypropylene (4) Cetyl Ether such as those sold as Nikkol PBC-34 from Nikko Chemicals Co., PPG-5 Ceteth-20; Polyoxyethylene (20) Polyoxypropylene (5) Cetyl Ether such as those sold as Procetyl AWS from Croda Inc., PPG-8 Ceteth-20; Polyoxyethylene (20) Polyoxypropylene (8) Cetyl Ether such as those sold as Nikkol PBC-44 from Nikko Chemicals Co., and PPG-23 Steareth-34; Polyoxyethylene Polyoxypropylene Stearyl Ether (34 EO) (23 PO) such as those sold as Unisafe 34S-23 from Pola Chemical Industries.

It is more preferable that the polyoxyethylenated (1-40 EO) and polyoxypropylenated (1-30 PO) alkyl ($C_{16}$-$C_{30}$) ethers be (15-40 EO) and polyoxypropylenated (5-30 PO) alkyl ($C_{16}$-$C_{24}$) ethers, which could be selected from the group consisting of PPG-6 Decyltetradeceth-30, PPG-13 Decyltetradeceth-24, PPG-6 Decyltetradeceth-20, PPG-5 Ceteth-20, PPG-8 Ceteth-20, and PPG-23 Steareth-34.

It is most preferable that the polyoxyethylenated (1-40 EO) and polyoxypropylenated (1-30 PO) alkyl ($C_{16}$-$C_{30}$) ethers be (15-40 EO) and polyoxypropylenated (5-30 PO) alkyl ($C_{16}$-$C_{24}$) ethers, which could be selected from the group consisting of PPG-6 Decyltetradeceth-30, PPG-13 Decyltetradeceth-24, PPG-5 Ceteth-20, and PPG-8 Ceteth-20. They can also provide a composition with transparency for a long time.

According to one of the embodiments of the present invention, the nonionic surfactant may be selected from copolymers of ethylene oxide and of propylene oxide, in particular copolymers of the following formula:

$$HO(C_2H_4O)_a(C_3H_6O)_b(C_2H_4O)_cH$$

in which a, b and c are integers such that a+c ranges from 2 to 100 and b ranges from 14 to 60, and mixtures thereof.

If the (c) polyoxyalkylenated organosilicon compound is not a polyoxyalkylenated silicone, the nonionic surfactant may be selected from silicone surfactants. Non-limiting mention may be made of those disclosed in documents U.S. Pat. Nos. 5,364,633 and 5,411,744.

The silicone surfactant may preferably be a compound of formula (I):

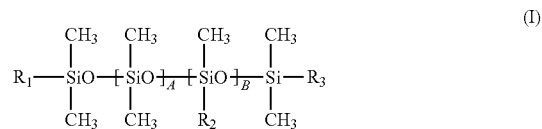

in which:

$R_1$, $R_2$ and $R_3$, independently of each other, represent a $C_1$-$C_6$ alkyl radical or a radical —$(CH_2)_x$—$(OCH_2CH_2)_y$—

$(OCH_2CH_2CH_2)_z$—$OR_4$, at least one radical $R_1$, $R_2$ or $R_3$ not being an alkyl radical; $R_4$ being a hydrogen, an alkyl radical or an acyl radical;

A is an integer ranging from 0 to 200;

B is an integer ranging from 0 to 50; with the proviso that A and B are not simultaneously equal to zero;

x is an integer ranging from 1 to 6;

y is an integer ranging from 1 to 30;

z is an integer ranging from 0 to 5.

According to one preferred embodiment of the present invention, in the compound of formula (I), the alkyl radical is a methyl radical, x is an integer ranging from 2 to 6 and y is an integer ranging from 4 to 30.

As examples of silicone surfactants of formula (I), mention may be made of the compounds of formula (II):

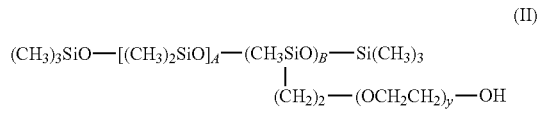

(II)

in which A is an integer ranging from 20 to 105, B is an integer ranging from 2 to 10 and y is an integer ranging from 10 to 20.

As examples of silicone surfactants of formula (I), mention may also be made of the compounds of formula (III):

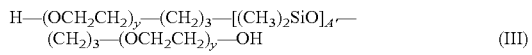

(III)

in which A' and y are integers ranging from 10 to 20.

Compounds of the present invention which may be used are those sold by the company Dow Corning under the names DC 5329, DC 7439-146, DC 2-5695 and Q4-3667. The compounds DC 5329, DC 7439-146 and DC 2-5695 are compounds of formula (II) in which, respectively, A is 22, B is 2 and y is 12; A is 103, B is 10 and y is 12; and A is 27, B is 3 and y is 12.

The compound Q4-3667 is a compound of formula (III) in which A is 15 and y is 13.

The amount of the (d) nonionic surfactant(s) other than the (b) polyglyceryl fatty acid ester in the composition according to the present invention may be 0.01% by weight or more, preferably 0.05% by weight or more, and more preferably 0.1% by weight or more, relative to the total weight of the composition. It may be even more preferable that the amount of the (d) nonionic surfactant(s) in the composition according to the present invention be 0.5% by weight or more, relative to the total weight of the composition.

On the other hand, the amount of the (d) nonionic surfactant(s) other than the (b) polyglyceryl fatty acid ester in the composition according to the present invention may be 20% by weight or less, preferably 15% by weight or less, and more preferably 10% by weight or less, relative to the total weight of the composition. It may be even more preferable that the amount of the (d) nonionic surfactant(s) in the composition according to the present invention be 5% by weight or less, relative to the total weight of the composition.

The amount of the (d) nonionic surfactant(s) other than the (b) polyglyceryl fatty acid ester(s) in the composition according to the present invention may range from 0.01 to 20% by weight, preferably from 0.05 to 15% by weight, more preferably from 0.1 to 10% by weight, relative to the total weight of the composition. It may be even more preferable that the amount of the (b) nonionic surfactant(s) in the composition according to the present invention be from 0.5% to 5% by weight, relative to the total weight of the composition.

[Anionic Surfactant]

The composition according to the present invention comprises (e) at least one anionic surfactant. A single type of anionic surfactant may be used, but two or more different types of anionic surfactants may be used in combination.

According to the present invention, the type of anionic surfactant is not limited. It is preferable that the anionic surfactant be selected from the group consisting of ($C_6$-$C_{30}$) alkyl sulfates, ($C_6$-$C_{30}$) alkyl ether sulfates, ($C_6$-$C_{30}$) alkylamido ether sulfates, alkylaryl polyether sulfates, monoglyceride sulfates; ($C_6$-$C_{30}$) alkylsulfonates, ($C_6$-$C_{30}$) alkylamide sulfonates, ($C_6$-$C_{30}$) alkylaryl sulfonates, α-olefin sulfonates, paraffin sulfonates; ($C_6$-$C_{30}$) alkyl phosphates; ($C_6$-$C_{30}$) alkyl sulfosuccinates, ($C_6$-$C_{30}$) alkyl ether sulfosuccinates, ($C_6$-$C_{30}$) alkylamide sulfosuccinates; ($C_6$-$C_{30}$) alkyl sulfoacetates; ($C_6$-$C_{24}$) acyl sarcosinates; ($C_6$-$C_{24}$) acyl glutamates; ($C_6$-$C_{30}$) alkylpolyglycoside carboxylic ethers; ($C_6$-$C_{30}$) alkylpolyglycoside sulfosuccinates; ($C_6$-$C_{30}$) alkyl sulfosuccinamates; ($C_6$-$C_{24}$) acyl isethionates; N—($C_6$-$C_{24}$) acyl taurates; $C_6$-$C_{30}$ fatty acid salts; coconut oil acid salts or hydrogenated coconut oil acid salts; ($C_8$-$C_{20}$) acyl lactylates; ($C_6$-$C_{30}$) alkyl-D-galactoside uronic acid salts; polyoxyalkylenated ($C_6$-$C_{30}$) alkyl ether carboxylic acid salts; polyoxyalkylenated ($C_6$-$C_{30}$) alkylaryl ether carboxylic acid salts; polyoxyalkylenated ($C_6$-$C_{30}$) alkylamido ether carboxylic acid salts; and polyoxyalkylenated ($C_6$-$C_{30}$) alkyl ether phosphates.

It is more preferable that the anionic surfactant be selected from salts of $C_6$-$C_{30}$ acyl glutamates such as sodium stearoyl glutamate, ($C_6$-$C_{24}$) acyl taurates such as sodium methyl stearoyl taurate, and mixtures thereof.

In at least one embodiment, the anionic surfactants are in the form of salts such as salts of alkali metals, for instance sodium; salts of alkaline-earth metals, for instance magnesium; ammonium salts; amine salts; and amino alcohol salts. Depending on the conditions, they may also be in acid form.

It should be noted that the alkyl or acyl radicals of these various compounds can contain from 12 to 20 carbon atoms. Moreover, for instance, the aryl radical can be chosen from a phenyl or benzyl group.

Furthermore, the polyoxyalkylenated anionic surfactants can, for example, comprise from 2 to 50 alkylene oxide, for instance ethylene oxide, groups.

In accordance with at least one embodiment of the present disclosure, the anionic surfactant can be chosen from stearic acid, dicetyl phosphate and ceteth-10 phosphate.

The amount of the (e) anionic surfactant(s) in the composition according to the present invention may be 0.001% by weight or more, preferably 0.005% by weight or more, and more preferably 0.01% by weight or more, relative to the total weight of the composition. It may be even more preferable that the amount of the (e) anionic surfactant(s) in the composition according to the present invention be 0.05% by weight or more, relative to the total weight of the composition.

On the other hand, the amount of the (e) anionic surfactant(s) in the composition according to the present invention may be 20% by weight or less, preferably 15% by weight or less, and more preferably 10% by weight or less, relative to the total weight of the composition. It may be even more preferable that the amount of the (e) anionic surfactant(s) in the composition according to the present invention be 5% by weight or less, relative to the total weight of the composition.

The amount of the (e) anionic surfactant(s) in the composition according to the present invention may range from 0.001 to 20% by weight, preferably from 0.005 to 15% by weight, and more preferably from 0.01 to 10% by weight, relative to the total weight of the composition. It may be even more preferable that the amount of the (e) anionic surfactant(s) in the composition according to the present invention be from 0.05% to 5% by weight, relative to the total weight of the composition.

[Water]

The composition according to the present invention may comprise water.

The amount of water is not limited, and may be from 40 to 95% by weight, preferably from 45 to 90% by weight, and more preferably 50 to 85% by weight, relative to the total weight of the composition.

The amount of water in the composition according to the present invention may be 50% by weight or more, preferably 55% by weight or more, and more preferably 60% by weight or more, relative to the total weight of the composition. It may be even more preferable that the amount of water in the composition according to the present invention be 65% by weight or more, relative to the total weight of the composition.

On the other hand, the amount of water in the composition according to the present invention may be 95% by weight or less, preferably 90% by weight or less, and more preferably 85% by weight or less, relative to the total weight of the composition. It may be even more preferable that the amount of water in the composition according to the present invention be 80% by weight or less, relative to the total weight of the composition.

The amount of water in the composition according to the present invention may range from 50 to 95% by weight, preferably from 55 to 90% by weight, more preferably from 60 to 85% by weight, relative to the total weight of the composition. It may be even more preferable that the amount of water in the composition according to the present invention be from 65% to 80% by weight, relative to the total weight of the composition.

[Additional Cationic/Amphoteric Surfactant]

The composition according to the present invention may further comprise at least one additional cationic and/or anionic surfactant. A single type of additional cationic and/or amphoteric surfactant may be used, but two or more different types of additional cationic and/or amphoteric surfactants may be used in combination.

The amount of the additional cationic and/or amphoteric surfactant(s) in the composition according to the present invention may range from 0.001 to 20% by weight, preferably from 0.005 to 15% by weight, and more preferably from 0.01 to 10% by weight, relative to the total weight of the composition. It may be even more preferable that the amount of water in the composition according to the present invention be from 0.05% to 5% by weight, relative to the total weight of the composition.

(Amphoteric Surfactants)

According to the present invention, the type of amphoteric surfactant is not limited. The amphoteric or zwitterionic surfactants can be, for example (non-limiting list), amine derivatives such as aliphatic secondary or tertiary amines, and optionally quaternized amine derivatives, in which the aliphatic radical is a linear or branched chain comprising 8 to 22 carbon atoms and containing at least one water-solubilizing anionic group (for example, carboxylate, sulfonate, sulfate, phosphate or phosphonate).

The amphoteric surfactant may preferably be selected from the group consisting of betaines and amidoaminecarboxylated derivatives.

The betaine-type amphoteric surfactant is preferably selected from the group consisting of alkylbetaines, alkylamidoalkylbetaines, sulfobetaines, phosphobetaines, and alkylamidoalkylsulfobetaines, in particular, ($C_8$-$C_{24}$) alkylbetaines, ($C_8$-$C_{24}$) alkylamido ($C_1$-$C_8$) alkylbetaines, sulfobetaines, and ($C_8$-$C_{24}$) alkylamido ($C_1$-$C_8$) alkylsulfobetaines. In one embodiment, the amphoteric surfactants of betaine type are chosen from ($C_8$-$C_{24}$) alkylbetaines, ($C_8$-$C_{24}$) alkylamido($C_1$-$C_8$) alkylsulfobetaines, sulfobetaines, and phosphobetaines.

Non-limiting examples that may be mentioned include the compounds classified in the CTFA dictionary, 9th edition, 2002, under the names cocobetaine, laurylbetaine, cetylbetaine, coco/oleamidopropylbetaine, cocamidopropylbetaine, palmitamidopropylbetaine, stearamidopropylbetaine, cocamidoethylbetaine, cocamidopropylhydroxysultaine, oleamidopropylhydroxysultaine, cocohydroxysultaine, laurylhydroxysultaine, and cocosultaine, alone or as mixtures.

The betaine-type amphoteric surfactant is preferably an alkylbetaine and an alkylamidoalkylbetaine, in particular cocobetaine and cocamidopropylbetaine.

Among the amidoaminecarboxylated derivatives, mention may be made of the products sold under the name Miranol, as described in U.S. Pat. Nos. 2,528,378 and 2,781,354 and classified in the CTFA dictionary, 3rd edition, 1982 (the disclosures of which are incorporated herein by reference), under the names Amphocarboxyglycinates and Amphocarboxypropionates, with the respective structures:

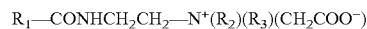

in which:

$R_1$ denotes an alkyl radical of an acid $R_1$—COOH present in hydrolysed coconut oil, a heptyl, nonyl or undecyl radical, $R_2$ denotes a beta-hydroxyethyl group, and $R_3$ denotes a carboxymethyl group; and

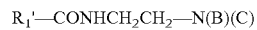

in which:

B represents —$CH_2CH_2OX'$,

C represents —$(CH_2)_z$—Y', with z=1 or 2,

X' denotes a —$CH_2CH_2$—COOH group, —$CH_2$—COOZ', —$CH_2CH_2$—COOH, —$CH_2CH_2$—COOZ' or a hydrogen atom, Y' denotes —COOH, —COOZ', —$CH_2$—CHOH—$SO_3Z'$ or a —$CH_2$—CHOH—$SO_3H$ radical, Z' represents an ion of an alkaline or alkaline earth metal such as sodium, an ammonium ion or an ion issued from an organic amine, and $R_1'$ denotes an alkyl radical of an acid $R_1'$—COOH present in coconut oil or in hydrolysed linseed oil, an alkyl radical, such as a $C_7$, $C_9$, $C_{11}$ or $C_{13}$ alkyl radical, a $C_{17}$ alkyl radical and its iso form, or an unsaturated $C_{17}$ radical.

It is preferable that the amphoteric surfactant be selected from ($C_8$-$C_{24}$) alkyl amphomonoacetates, ($C_8$-$C_{24}$) alkyl amphodiacetates, ($C_8$-$C_{24}$) alkyl amphomonopropionates, and ($C_8$-$C_{24}$) alkyl amphodipropionates.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphopropionate, Disodium Caprylamphodipropionate, Disodium Caprylamphodipropionate, Lauroamphodipropionic acid and Cocoamphodipropionic acid.

By way of example, mention may be made of the cocoamphodiacetate sold under the trade name Miranol® C2M concentrate by the company Rhodia Chimie.

(Cationic Surfactants)

According to the present invention, the type of cationic surfactant is not limited. The cationic surfactant may be selected from the group consisting of optionally polyoxyalkylenated, primary, secondary or tertiary fatty amine salts, quaternary ammonium salts, and mixtures thereof.

Examples of quaternary ammonium salts that may be mentioned include, but are not limited to: those of general formula (I) below:

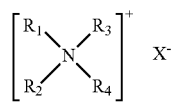
(I)

wherein
$R_1$, $R_2$, $R_3$, and $R_4$, which may be identical or different, are chosen from linear and branched aliphatic radicals comprising from 1 to 30 carbon atoms and optionally comprising heteroatoms such as oxygen, nitrogen, sulfur and halogens. The aliphatic radicals may be chosen, for example, from alkyl, alkoxy, $C_2$-$C_6$ polyoxyalkylene, alkylamide, ($C_{12}$-$C_{22}$) alkylamido ($C_2$-$C_6$) alkyl, ($C_{12}$-$C_{22}$) alkylacetate and hydroxyalkyl radicals; and aromatic radicals such as aryl and alkylaryl; and $X^-$ is chosen from halides, phosphates, acetates, lactates, ($C_2$-$C_6$) alkyl sulfates and alkyl- or alkylaryl-sulfonates;

quaternary ammonium salts of imidazoline, for instance those of formula (II) below:

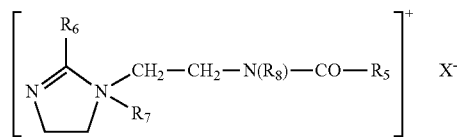
(II)

wherein:
$R_5$ is chosen from alkenyl and alkyl radicals comprising from 8 to 30 carbon atoms, for example fatty acid derivatives of tallow or of coconut;
$R_6$ is chosen from hydrogen, $C_1$-$C_4$ alkyl radicals, and alkenyl and alkyl radicals comprising from 8 to 30 carbon atoms;
$R_7$ is chosen from $C_1$-$C_4$ alkyl radicals;
$R_8$ is chosen from hydrogen and $C_1$-$C_4$ alkyl radicals; and
$X^-$ is chosen from halides, phosphates, acetates, lactates, alkyl sulfates, alkyl sulfonates, and alkylaryl sulfonates. In one embodiment, $R_5$ and $R_6$ are, for example, a mixture of radicals chosen from alkenyl and alkyl radicals comprising from 12 to 21 carbon atoms, such as fatty acid derivatives of tallow, $R_7$ is methyl and $R_8$ is hydrogen. Examples of such products include, but are not limited to, Quaternium-27 (CTFA 1997) and Quaternium-83 (CTFA 1997), which are sold under the names "Rewoquat®" W75, W90, W75PG and W75HPG by the company Witco; diquaternary ammonium salts of formula (III):

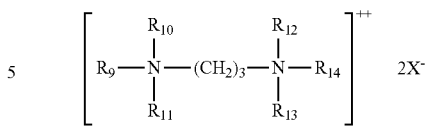
(III)

wherein:
$R_9$ is chosen from aliphatic radicals comprising from 16 to 30 carbon atoms;
$R_{10}$ is chosen from hydrogen or alkyl radicals comprising from 1 to 4 carbon atoms or a group $(R_{16a})(R_{17a})(R_{18a})N^+$ $(CH_2)_3$;
$R_{11}$, $R_{12}$, $R_{13}$, $R_{14}$, $R_{16a}$, $R_{17a}$, and $R_{18a}$, which may be identical or different, are chosen from hydrogen and alkyl radicals comprising from 1 to 4 carbon atoms; and
$X^-$ is chosen from halides, acetates, phosphates, nitrates, ethyl sulfates, and methyl sulfates.

An example of one such diquaternary ammonium salt is FINQUAT CT-P of FINETEX (Quaternium-89) or FINQUAT CT of FINETEX (Quaternium-75); and quaternary ammonium salts comprising at least one ester function, such as those of formula (IV) below:

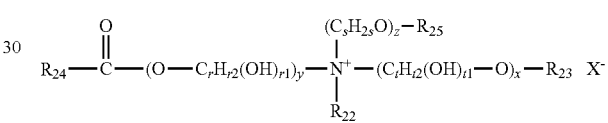
(IV)

wherein:
$R_{22}$ is chosen from $C_1$-$C_6$ alkyl radicals and $C_1$-$C_6$ hydroxyalkyl and dihydroxyalkyl radicals;
$R_{23}$ is chosen from:
the radical below:

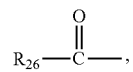

linear and branched, saturated and unsaturated $C_1$-$C_{22}$ hydrocarbon-based radicals $R_{27}$, and hydrogen,
$R_{25}$ is chosen from:
the radical below:

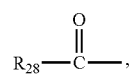

linear and branched, saturated and unsaturated $C_1$-$C_6$ hydrocarbon-based radicals $R_{29}$, and hydrogen,
$R_{24}$, $R_{26}$, and $R_{28}$, which may be identical or different, are chosen from linear and branched, saturated and unsaturated, $C_7$-$C_{21}$, hydrocarbon-based radicals;
r, s, and t, which may be identical or different, are chosen from integers ranging from 2 to 6; each of r1 and t1, which may be identical or different, is 0 or 1, and r2+r1=2r and t1+2t=2t;
y is chosen from integers ranging from 1 to 10;
x and z, which may be identical or different, are chosen from integers ranging from 0 to 10;

$X^-$ is chosen from simple and complex, organic and inorganic anions; with the proviso that the sum x+y+z ranges from 1 to 15, that when x is 0, $R_{23}$ denotes $R_{27}$, and that when z is 0, $R_{25}$ denotes $R_{29}$. $R_{22}$ may be chosen from linear and branched alkyl radicals. In one embodiment, $R_{22}$ is chosen from linear alkyl radicals. In another embodiment, $R_{22}$ is chosen from methyl, ethyl, hydroxyethyl, and dihydroxypropyl radicals, for example methyl and ethyl radicals. In one embodiment, the sum x+y+z ranges from 1 to 10. When $R_{23}$ is a hydrocarbon-based radical $R_{27}$, it may be long and comprise from 12 to 22 carbon atoms, or short and comprise from 1 to 3 carbon atoms. When $R_{25}$ is a hydrocarbon-based radical $R_{29}$, it may comprise, for example, from 1 to 3 carbon atoms. By way of a non-limiting example, in one embodiment, $R_{24}$, $R_{26}$, and $R_{28}$, which may be identical or different, are chosen from linear and branched, saturated and unsaturated, $C_{11}$-$C_{21}$ hydrocarbon-based radicals, for example from linear and branched, saturated and unsaturated $C_{11}$-$C_{21}$ alkyl and alkenyl radicals. In another embodiment, x and z, which may be identical or different, are 0 or 1. In one embodiment, y is equal to 1. In another embodiment, r, s and t, which may be identical or different, are equal to 2 or 3, for example equal to 2. The anion $X^-$ may be chosen from, for example, halides, such as chloride, bromide, and iodide; and $C_1$-$C_4$ alkyl sulfates, such as methyl sulfate. However, methanesulfonate, phosphate, nitrate, tosylate, an anion derived from an organic acid, such as acetate and lactate, and any other anion that is compatible with the ammonium comprising an ester function, are other non-limiting examples of anions that may be used according to the present invention. In one embodiment, the anion $X^-$ is chosen from chloride and methyl sulfate.

In another embodiment, the ammonium salts of formula (IV) may be used, wherein:

$R_{22}$ is chosen from methyl and ethyl radicals,
x and y are equal to 1;
z is equal to 0 or 1;
r, s and t are equal to 2;
$R_{23}$ is chosen from:
the radical below:

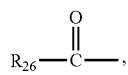

methyl, ethyl, and $C_{14}$-$C_{22}$ hydrocarbon-based radicals, and hydrogen;
$R_{25}$ is chosen from:
the radical below:

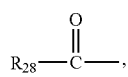

and hydrogen;
$R_{24}$, $R_{26}$, and $R_{28}$, which may be identical or different, are chosen from linear and branched, saturated and unsaturated, $C_{13}$-$C_{17}$ hydrocarbon-based radicals, for example from linear and branched, saturated and unsaturated, $C_{13}$-$C_{17}$ alkyl and alkenyl radicals.

In one embodiment, the hydrocarbon-based radicals are linear.

Non-limiting examples of compounds of formula (IV) that may be mentioned include salts, for example chloride and methyl sulfate, of diacyloxyethyl-dimethylammonium, of diacyloxyethyl-hydroxyethyl-methylammonium, of monoacyloxyethyl-dihydroxyethyl-methylammonium, of triacyloxyethyl-methylammonium, of monoacyloxyethyl-hydroxyethyl-dimethylammonium, and mixtures thereof. In one embodiment, the acyl radicals may comprise from 14 to 18 carbon atoms, and may be derived, for example, from a plant oil, for instance palm oil and sunflower oil. When the compound comprises several acyl radicals, these radicals may be identical or different.

These products may be obtained, for example, by direct esterification of optionally oxyalkylenated triethanolamine, triisopropanolamine, alkyldiethanolamine or alkyldiisopropanolamine onto fatty acids or onto mixtures of fatty acids of plant or animal origin, or by transesterification of the methyl esters thereof. This esterification may be followed by a quaternization using an alkylating agent chosen from alkyl halides, for example methyl and ethyl halides; dialkyl sulfates, for example dimethyl and diethyl sulfates; methyl methanesulfonate; methyl para-toluenesulfonate; glycol chlorohydrin; and glycerol chlorohydrin.

Such compounds are sold, for example, under the names Dehyquart® by the company Cognis, Stepanquat® by the company Stepan, Noxamium® by the company Ceca, and "Rewoquat® WE 18" by the company Rewo-Goldschmidt.

Other non-limiting examples of ammonium salts that may be used in the compositions according to the present invention include the ammonium salts comprising at least one ester function described in U.S. Pat. Nos. 4,874,554 and 4,137,180.

The quaternary ammonium salts mentioned above that may be used in compositions according to the present invention include, but are not limited to, those corresponding to formula (I), for example tetraalkylammonium chlorides, for instance dialkyldimethylammonium and alkyltrimethylammonium chlorides in which the alkyl radical comprises from about 12 to 22 carbon atoms, such as behenyltrimethylammonium, distearyldimethylammonium, cetyltrimethylammonium and benzyldimethylstearylammonium chloride; palmitylamidopropyltrimethylammonium chloride; and stearamidopropyldimethyl(myristyl acetate) ammonium chloride, sold under the name "Ceraphyl® 70" by the company Van Dyk.

According to one embodiment, the cationic surfactant that may be used in the compositions of the present invention is chosen from quaternary ammonium salts, for example from behenyltrimethylammonium chloride, cetyltrimethylammonium chloride, Quaternium-83, Quaternium-87, Quaternium-22, behenylamidopropyl-2,3-dihydroxypropyldimethylammonium chloride, palmitylamidopropyltrimethylammonium chloride, and stearamidopropyldimethylamine.

[Cosmetic Active Ingredients]

The composition according to the present invention may further comprise at least one cosmetic active ingredient. A single type of cosmetic active ingredient may be used, but two or more different types of cosmetic active ingredient may be used in combination.

It is preferable that the cosmetic active ingredient be selected from the group consisting of whitening agents, anti-aging agents, UV filters, keratolytic and anti-bacterial agents.

It is preferable that the cosmetic active ingredient be selected from the group consisting of oxothiazolidinecarboxylic acid, Vitamin B3 and derivatives thereof, preferably niacinamide, Vitamin C and derivatives thereof, preferably 3-O-ethyl ascorbic acid, resorcinol and derivatives thereof such as phenylethyl resorcinol, xanthine bases, preferably caffeine, camphor benzalkonium methosulfate, ellagic acid, hydroxyphenoxy propionic acid, diethyllutidinate, terephthalylidene dicamphor sulfonic acid, ferulic acid, salicylic acid, phloretine, acetyl trifluoromethylphenyl valylglycine, resveratrol, apigenin, prasterone, benzophenone-3, butyl methoxydibenzoylmethane, capryloyl salicylic acid, ethylhexyl salicylate, and jasmonic acid derivatives, preferably sodium tetrahydrojasmonate.

The cosmetic active ingredient may be present in an amount ranging from 0.001% to 10% by weight, and preferably from 0.01% to 5% by weight, such as from 0.1% to 1% by weight, relative to the total weight of the composition.

[Polyol]

The composition according to the present invention may further comprise at least one polyol. A single type of polyol may be used, but two or more different types of polyol may be used in combination.

The term "polyol" here means an alcohol having two or more hydroxy groups, and does not encompass a saccharide or a derivative thereof. The derivative of a saccharide includes a sugar alcohol which is obtained by reducing one or more carbonyl groups of a saccharide, as well as a saccharide or a sugar alcohol in which the hydrogen atom or atoms in one or more hydroxy groups thereof has or have been replaced with at least one substituent such as an alkyl group, a hydroxyalkyl group, an alkoxy group, an acyl group or a carbonyl group.

The polyol may be a $C_2$-$C_{12}$ polyol, preferably a $C_2$-$C_9$ polyol, comprising at least 2 hydroxy groups, and preferably 2 to 5 hydroxy groups.

The polyol may be a natural or synthetic polyol. The polyol may have a linear, branched or cyclic molecular structure.

The polyol may be selected from glycerins and derivatives thereof, and glycols and derivatives thereof. The polyol may be selected from the group consisting of glycerin, diglycerin, polyglycerin, ethyleneglycol, diethyleneglycol, propyleneglycol, dipropyleneglycol, butyleneglycol, pentyleneglycol, hexyleneglycol, 1,3-propanediol, 1,5-pentanediol, polyethyleneglycol (5 to 50 ethyleneoxide groups), and sugars such as sorbitol.

The polyol may be present in an amount ranging from 0.01% to 30% by weight, and preferably from 0.1% to 20% by weight, such as from 1% to 10% by weight, relative to the total weight of the composition.

[Other Ingredients]

The composition according to the present invention may also comprise an effective amount of other ingredients, known previously elsewhere in lightening or coloring compositions, such as various common adjuvants, sequestering agents such as EDTA and etidronic acid, preserving agents, vitamins or provitamins different from those mentioned above, for instance, panthenol, opacifiers, fragrances, plant extracts, cationic polymers and so on.

The composition according to the present invention may further comprise at least one organic solvent. So the organic solvent is preferably water miscible. As the organic solvent, there may be mentioned, for example, $C_1$-$C_4$ alkanols, such as ethanol and isopropanol; aromatic alcohols such as benzyl alcohol and phenoxyethanol; analogous products; and mixtures thereof.

The organic water-soluble solvents may be present in an amount ranging from less than 10% by weight, preferably from 5% by weight or less, and more preferably from 1% by weight or less, relative to the total weight of the composition.

[Preparation and Properties]

The composition according to the present invention can be prepared by mixing the above essential and optional ingredients in accordance with a conventional process. The conventional process includes mixing with a homogenizer, for example a turbine mixer.

It may be preferable that the weight ratio of
(the total amounts of the (b) polyglyceryl fatty acid ester(s) and the (d) nonionic surfactant(s) other than the (b) polyglyceryl fatty acid ester(s))/the amount of the (a) oil(s)
in the composition according to the present invention be 1.0 or more, preferably 1.5 or more, and more preferably 2.0 or more, and preferably 10 or less, more preferably 5 or less.

It may also be preferable that the weight ratio of
the amount of the (c) polyoxyalkylenated organosilicon compound(s)/the amount of the (b) polyglyceryl fatty acid ester (s)
in the composition according to the present invention be 3.5 or more, preferably 4.0 or more, and more preferably 4.5 or more, and preferably 15 or less, more preferably 12 or less.

It is preferable that the composition according to the present invention be in the form of a nano- or micro-emulsion.

It is more preferable that the composition according to the present invention be in the form of an O/W nano- or micro-emulsion.

The "micro-emulsion" may be defined in two ways, namely, in a broad sense and in a narrow sense. That is to say, there is the one case ("micro-emulsion in the narrow sense") in which the micro-emulsion refers to a thermodynamically stable isotropic single liquid phase containing a ternary system having three ingredients of an oily component, an aqueous component and a surfactant, and there is the other case ("micro-emulsion in the broad sense") in which among thermodynamically unstable typical emulsion systems the micro-emulsion additionally includes those such emulsions presenting transparent or translucent appearances due to their smaller particle sizes (Satoshi Tomomasa, et al., Oil Chemistry, Vol. 37, No. 11 (1988), pp. 48-53). The "micro-emulsion" as used herein refers to a "micro-emulsion in the narrow sense", i.e., a thermodynamically stable isotropic single liquid phase.

The micro-emulsion refers to either one state of an O/W (oil-in-water) type microemulsion in which oil is solubilized by micelles, a W/O (water-in-oil) type microemulsion in which water is solubilized by reverse micelles, or a bicontinuous microemulsion in which the number of associations of surfactant molecules are rendered infinite so that both the aqueous phase and oil phase have a continuous structure.

The micro-emulsion may have a dispersed phase with a number average diameter of 100 nm or less, preferably 50 nm or less, and more preferably 20 nm or less, measured by laser granulometry.

The "nano-emulsion" here means an emulsion characterized by a dispersed phase with a size of less than 350 nm, the dispersed phase being stabilized by a crown of the (b) and (d) nonionic surfactant that may optionally form a liquid crystal phase of lamellar type, at the dispersed phase/continuous phase interface. In the absence of specific opacifiers, the transparency of the nano-emulsions arises from the small size of the dispersed phase, this small size being obtained by virtue of the use of mechanical energy and especially a high-pressure homogenizer.

Nanoemulsions can be distinguished from microemulsions by their structure. Specifically, micro-emulsions are thermodynamically stable dispersions formed from, for example, the (b) and (d) nonionic surfactant micells swollen with the (a) oil. Furthermore, microemulsions do not require substantial mechanical energy in order to be prepared.

The nano-emulsion may have a dispersed phase with a number average diameter of 300 nm or less, preferably 200 nm or less, and more preferably 100 nm or less, measured by laser granulometry.

[Process and Use]

It is preferable that the composition according to the present invention be a cosmetic composition, preferably a cosmetic composition for a keratin substance such as skin.

The composition according to the present invention can be used for a non-therapeutic process, such as a cosmetic process, for treating a keratin substance such as skin, hair, mucous membranes, nails, eyelashes, eyebrows and/or scalp, by being applied to the keratin substance.

Thus, the present invention also relates to a cosmetic process for treating a keratin substance, comprising the step of applying the composition according to the present invention to the keratin substance.

The present invention may also relate to a use of the composition according to the present invention as a cosmetic product or in a cosmetic product such as care products, washing products, make-up products, make-up-removing products, for body and/or facial skin and/or mucous membranes and/or the scalp and/or the hair and/or the nails and/or the eyelashes and/or the eyebrows.

In other words, the composition according to the present invention can be used, as it is, as a cosmetic product. Alternatively, the composition according to the present invention can be used as an element of a cosmetic product. For example the composition according to the present invention can be added to or combined with any other elements to form a cosmetic product.

The care product may be a lotion, a cream, a hair tonic, a hair conditioner, a sun screening agent, and the like. The washing product may be a shampoo, a face wash, a hand wash and the like. The make-up product may be a foundation, a mascara, a lipstick, a lip gloss, a blusher, an eye shadow, a nail varnish, and the like. The make-up-removing product may be a make-up cleansing agent and the like.

EXAMPLES

The present invention will be described in more detail by way of examples, which however should not be construed as limiting the scope of the present invention.

Examples 1-6 and Comparative Examples 1-5

The following compositions according to Examples 1-6 and Comparative Examples 1-5, shown in Table 1, were prepared by mixing the components shown in Table 1 as follows:

(1) mixing the ingredients of Phase A at 75-80° C. to form a uniform mixture of Phase A ingredients;
(2) mixing the ingredients of Phase B at 75-80° C. to form a uniform mixture of Phase B ingredients;
(3) adding the mixture of Phase B ingredients to the mixture of Phase A at 75-80° C., followed by mixing and maintaining the obtained mixture (Phases A and B) at 65-70° C.;
(4) mixing the ingredients of Phase C at room temperature to form a mixture of Phase C ingredients;
(5) adding the mixture of Phase C ingredients to the mixture of phase A and B ingredients at 65-70° C., followed by homogenizing them to obtain a uniform mixture (Phases A, B and C) and cooling the obtained mixture to about 30° C.;
(6) adding the ingredient of Phase D to the obtained uniform mixture (Phases A, B and C) followed by homogenizing to obtain a uniform mixture (Phases A, B, C and D); and
(7) adding the ingredient of Phase E to the obtained uniform mixture (Phases A, B, C and D) followed by homogenizing to obtain a uniform mixture (Phases A, B, C, D and E).

The numerical values for the amounts of the components shown in Table 1 are all based on "% by weight" as active raw materials.

TABLE 1

| Phase | Ingredients | Ex. 1 | Ex. 2 | Ex. 3 | Ex. 4 | Ex. 5 | Ex. 6 | Comp. Ex. 1 | Comp. Ex. 2 | Comp. Ex. 3 | Comp. Ex. 4 | Comp. Ex. 5 |
|---|---|---|---|---|---|---|---|---|---|---|---|---|
| A | Sodium Hydroxide | 0.005 | 0.005 | 0.005 | 0.005 | 0.005 | 0.005 | 0.005 | 0.005 | 0.005 | 0.005 | 0.005 |
|   | Disodium EDTA | 0.1 | 0.1 | 0.1 | 0.1 | 0.1 | 0.1 | 0.1 | 0.1 | 0.1 | 0.1 | 0.1 |
|   | Phenoxyethanol | 0.5 | 0.5 | 0.5 | 0.25 | 0.25 | 0.5 | 0.5 | 0.5 | 0.5 | 0.5 | 0.5 |
|   | Chlorphenesin | 0.3 | 0.3 | 0.3 | 0.3 | 0.3 | — | 0.3 | 0.3 | 0.3 | 0.3 | 0.3 |
|   | Glycerin | 2 | 5 | 5 | 5 | 5 | 8 | 2 | 2 | 2 | 2 | 2 |
|   | Propanediol | 5 | — | — | — | — | — | 5 | 5 | 5 | 5 | 5 |
|   | Methyl Gluceth-10 | 3 | 3 | 3 | 3 | 3 | 0.6 | 3 | 3 | 3 | 3 | 3 |
|   | (c) Bis-PEG-18 Methyl Ether Dimethyl Silane | 5 | 5 | 5 | 3.5 | 3.5 | 1.6 | 5 | 5 | — | 5 | 5 |
|   | (e) Sodium Methyl Stearoyl Taurate | 0.1 | 0.1 | 0.2 | 0.2 | 0.2 | 0.2 | 0.1 | 0.1 | 0.1 | 0.1 | — |
| B | (a) Ethylhexyl Palmitate | 0.5 | 0.5 | 0.5 | — | 0.5 | 0.3 | — | 0.5 | 0.5 | 0.5 | 0.5 |
|   | (a) Isopropyl Lauroyl Sarcosinate | 0.5 | 0.5 | 0.5 | 0.3 | 0.5 | — | — | 0.5 | 0.5 | 0.5 | 0.5 |
|   | (d) PPG-6 Decyltetradeceth-30 | 1 | 1 | 1 | 1 | 1 | 1 | 1 | 1 | 1 | — | 1 |
|   | (b) Polyglyceryl-5 Laurate | 1 | 1 | 1 | 0.3 | 1 | 0.3 | 1 | — | 1 | 1 | 1 |
|   | (f) Capryloyl Salicylic Acid | 0.1 | 0.3 | 0.3 | 0.1 | 0.1 | — | 0.1 | 0.1 | 0.1 | 0.1 | 0.1 |
|   | (f) Phenylethyl Resorcinol | 0.3 | — | 0.3 | — | — | 0.3 | 0.3 | 0.3 | 0.3 | 0.3 | 0.3 |
|   | Tocopherol | 0.1 | 0.1 | — | — | — | 0.1 | 0.1 | 0.1 | 0.1 | 0.1 | 0.1 |
| C | Xanthan Gum | 0.1 | 0.15 | 0.15 | 0.15 | 0.15 | 0.11 | 0.1 | 0.1 | 0.1 | 0.1 | 0.1 |
|   | Butylene Glycol | 5 | 5 | 5 | 5 | 5 | 5 | 5 | 5 | 5 | 5 | 5 |
| E | Ethanol | 5 | 5 | — | 2 | 2 | 3 | 5 | 5 | 5 | 5 | 5 |
| A, D | Water | qsp100 | qsp100 | qsp100 | qsp100 | qsp100 | qsp100 | qsp100 | qsp100 | qsp100 | qsp100 | qsp100 |

[Evaluations]

(Non-Sticky Feeling after Application)

5 professional panelists evaluated "non-sticky feeling after application" for the compositions according to Examples 1-6 and Comparative Examples 1-5. Each panelist took each composition in their hands, then applied it onto their faces to evaluate non-sticky feeling after application, and graded it from 1 (poor) to 5 (very good), which was then classified in the following 4 categories based on the average of the grade:

Very Good: From 5.0 to 4.0
Good: From 3.9 to 3.0
Poor: From 2.9 to 2.0
Very Poor: From 1.9 to 1.0

The results are shown in Tables 2 and 3 below.

(Stability)

(1) Immediately after Preparation

Each of the compositions according to Examples 1-6 and Comparative Examples 1-5 was evaluated immediately after the preparation of each composition, in terms of the emulsion state by visual and microscopic observation, and was evaluated in accordance with the following criteria:

Very Good: Transparent aspect was observed.
Good: Very slight translucent aspect was observed.
Poor: Turbid aspect was clearly observed.
Very Poor: Very turbid aspect was remarkably observed.

The results are shown in Tables 2 and 3 below.

(2) 2 Months Later at 45° C.

Each of the compositions according to Examples 1-6 and Comparative Examples 1-5 was filled into a glass bottle and was held under temperature conditions of 45° C. for 2 months. Each sample was then investigated for the degree of change (transparency, color, odor, and pH), and evaluated in accordance with the following criteria:

Very Good: Almost the same conditions as at production.
Good: Changes in transparency color, odor, and pH were somewhat observed. However, no separation and no turbid aspect were observed. Transparency was almost maintained.
Poor: Changes in transparency, color, odor, and pH were clearly observed. Separation and turbid aspect were clearly observed.
Very Poor: Changes in transparency, color, odor, and pH were remarkably noticed. Separation and turbid aspect were remarkably noticed.

The results are shown in Tables 2 and 3 below.

TABLE 2

|  | Ex. 1 | Ex. 2 | Ex. 3 | Ex. 4 | Ex. 5 | Ex. 6 |
|---|---|---|---|---|---|---|
| Non-Sticky Feeling After Application | Very Good | Very Good | Very Good | Very Good | Good | Very Good |
| Stability Immediately After Preparation | Very Good | Very Good | Very Good | Very Good | Very Good | Very Good |
| 2 Months Later at 45° C. | Very Good | Very Good | Very Good | Very Good | Very Good | Very Good |

TABLE 3

|  | Comp. Ex. 1 | Comp. Ex. 2 | Comp. Ex. 3 | Comp. Ex. 4 | Comp. Ex. 5 |
|---|---|---|---|---|---|
| Non-Sticky Feeling After Application | Good | Good | Very Poor | Good | Good |
| Stability Immediately After Preparation | Poor | Very Poor | Good | Poor | Poor |
| 2 Months Later at 45° C. | Poor | Very Poor | Good | Poor | Very Poor |

As is clear from Tables 1-3, the composition in the form of an O/W emulsion according to the present invention (Examples 1-6) can provide both a non-sticky feeling after application and stability immediately after preparation and 2 months later at higher temperature, due to the combination of a polyglyceryl fatty acid ester (e.g., polyglyceryl-5 laurate), a polyoxyalkylenated organosilicon compound (e.g., Bis-PEG-18 methyl ether dimethyl silane), a nonionic surfactant (e.g., PPG-6 decyltetradeceth-30) and an anionic surfactant (e.g., sodium methyl stearoyl taurate). Thus, the composition according to the present invention can provide an excellent feeling to the touch and stability even after a long time period.

On the other hand, Comparative Example 1 which lacks oil ingredients, does not show excellent stability. Also, Comparative Example 2, which lacks polyglyceryl fatty acid ester, does not show excellent stability. Comparative Example 3, which lacks polyoxyalkylenated organosilicon compound, does not show an excellent feeling to the touch. Comparative Example 4, which lacks a nonionic surfactant other than a polyglyceryl fatty acid ester, does not show stability over time. Also, Comparative Example 5, which lacks an anionic surfactant, does not show stability over time.

The invention claimed is:

1. A composition comprising:
   (a) at least one oil;
   (b) at least one polyglyceryl fatty acid monoester;
   (c) at least one polyoxyalkylenated organosilicon compound;
   (d) at least one nonionic surfactant other than the (b) polyglyceryl fatty acid monoester; and
   (e) at least one anionic surfactant,
   wherein the (c) polyoxyalkylenated organosilicon compound is selected from polyoxyalkylenated silanes, and the composition is transparent or translucent and wherein the composition in a form of an O/W (oil-in-water) nano- or micro-emulsion.

2. The composition according to claim 1, wherein the (a) oil comprises at least one ester oil.

3. The composition according to claim 1, wherein the amount of the (a) oil in the composition ranges from 0.01 to 30% by weight, relative to the total weight of the composition.

4. The composition according to claim 1, wherein the (b) polyglyceryl fatty acid monoester has a polyglyceryl moiety derived from 2 to 10 glycerins.

5. The composition according to claim 1, wherein the (b) polyglyceryl fatty acid monoester is chosen from polyglyceryl monolaurate comprising 2 to 6 glycerol units, polyglyceryl mono(iso)stearate comprising 2 to 6 glycerol units, and polyglyceryl monooleate comprising 2 to 6 glycerol units.

6. The composition according to claim 1, wherein the amount of the (b) polyglyceryl fatty acid monoester in the composition ranges from 0.01 to 20% by weight, relative to the total weight of the composition.

7. The composition according to claim 1, wherein the amount of the (c) polyoxyalkylenated organosilicon compound in the composition ranges from 0.01 to 20% by weight, relative to the total weight of the composition.

8. The composition according to claim 1, wherein the (d) nonionic surfactant is selected from polyoxyethylenated (1-40 EO) and polyoxypropylenated (1-30 PO) alkyl ($C_{16}$-$C_{30}$) ethers.

9. The composition according to claim 1, wherein the amount of the (d) nonionic surfactant in the composition ranges from 0.01 to 20% by weight, relative to the total weight of the composition.

10. The composition according to claim 1, wherein the amount of the (e) anionic surfactant in the composition ranges from 0.001 to 20% by weight, relative to the total weight of the composition.

11. The composition according to claim 1, wherein the weight ratio of (the total amounts of the (b) polyglyceryl fatty acid monoester(s) and the (d) nonionic surfactant(s) other than the (b) polyglyceryl fatty acid monoester(s))/the amount of the (a) oil(s) is 1.0 or more.

12. The composition according to claim 1, wherein the weight ratio of the amount of the (c) polyoxyalkylenated organosilicon compound(s)/the amount of the (b) polyglyceryl fatty acid monoester(s) is 3.5 or more.

13. A cosmetic process for treating a keratin substance, comprising:

applying the composition according to claim 1 to the keratin substance.

14. The composition according to claim 1, wherein the composition is transparent.

\* \* \* \* \*